017
United States Patent [19]

d'Hinterland et al.

[11] 4,397,838

[45] Aug. 9, 1983

[54] PREPARATIONS OF PURIFIED BACTERIAL MEMBRANAL PROTEOGLYCANS

[75] Inventors: Lucien D. d'Hinterland; Gérard Normier; Anne-Marie Pinel; Jacques Durand, all of Castres, France

[73] Assignee: Pierre Fabre S.A., Paris, France

[21] Appl. No.: 280,379

[22] Filed: Jul. 6, 1981

Related U.S. Application Data

[62] Division of Ser. No. 103,202, Dec. 13, 1979, Pat. No. 4,297,272.

[30] Foreign Application Priority Data

Dec. 19, 1978 [FR] France ................................ 78 35649

[51] Int. Cl.³ .................. A61K 39/00; A61K 39/102; A61K 39/09; C07G 7/00
[52] U.S. Cl. ................................ 424/92; 260/112 R; 424/88
[58] Field of Search .................................. 424/88–92; 260/112 R

[56] References Cited

U.S. PATENT DOCUMENTS

| 3,855,197 | 12/1974 | Hirsch et al. | 424/92 |
|---|---|---|---|
| 4,036,953 | 7/1977 | Adam et al. | 424/92 |
| 4,042,678 | 8/1977 | Corbaru et al. | 424/92 |
| 4,069,314 | 1/1978 | Adlam et al. | 424/92 |
| 4,094,971 | 6/1978 | Chedid et al. | 424/92 |

FOREIGN PATENT DOCUMENTS

| 822817 | 5/1975 | Belgium . |
|---|---|---|
| 839893 | 9/1976 | Belgium . |
| 2253499 | 7/1975 | France . |

Primary Examiner—Blondel Hazel
Attorney, Agent, or Firm—Maky, Renner, Otto & Boisselle

[57] ABSTRACT

This invention relates to a process for the preparation of purified bacterial membranal proteoglycans. The process comprises at least one step in which crude proteoglycans are treated in aqueous medium with a base or a hypobromite, followed by elimination of the excess reactant and the insoluble residue, the purified proteoglycans being present in aqueous solution. The thus obtained purified proteoglycans may be used as immunity adjuvants in vaccines without causing side-effects such as pyrogenic reactions.

14 Claims, No Drawings

PREPARATIONS OF PURIFIED BACTERIAL MEMBRANAL PROTEOGLYCANS

This is a division of application Ser. No. 103,202, filed Dec. 13, 1979 now U.S. Pat. No. 4,297,272.

The present invention relates to purified and detoxified bacterial membranal proteoglycans, to a process for their preparation and to their use as immunity adjuvants in vaccines.

Vaccines are generally formed by one or more immunogenic elements, i.e. elements capable of producing an immunity reaction, but in some cases the immunogenic elements are incapable of developing their immunogenic power on their own or only develop it to a minimal extent, so that it is necessary in such cases to use products known as "immunity adjuvants".

Conventionally, immunity adjuvants are products which have an immunostimulating activity without being immunogenic themselves. One example is the immunity adjuvant known as incomplete Freund's adjuvant (IFA) which consists of 85% paraffin and 15% naphthalene.

The present invention relates to immunity adjuvants for use in vaccines and, more particularly, for use in so-called ribosomal vaccines or vaccines based on RNA. Ribosomal vaccines of this type are described, in particular, in French Pat. No. 73 43 957.

The vaccines in question contain as their immunogenic compound either bacterial ribosomes or bacterial RNA's emanating from pathogenic bacteria against which it is desired to obtain immunity. However, as described in the above-mentioned French Patent, these immunogenic compounds are only capable of developing their full activity in the presence of immunity adjuvants formed by membranal proteoglycans extracted from membranes of bacteria.

Conventional processes for the preparation of these proteoglycans do not, however, enable these proteoglycans to be completely purified and detoxified, and in some cases this can give rise to vaccinal or pyrogenic reactions which reactions it is advantageous to be able to avoid.

More particularly therefore, the present invention relates to a process for purifying such proteoglycans to obtain bacterial membranal proteoglycans which are soluble in water. This represents a considerable advantage because the proteoglycans thus obtained may be sterilised simply by filtration and this obviates the need to use heat which, hitherto, has been in danger of denaturing their properties. It is for this reason that, in the context of the present invention, purified proteoglycans are understood to be proteoglycans which are soluble in water.

Accordingly, the present invention provides a process for the preparation of purified, soluble, bacterial membranal proteoglycans which comprises at least one step in which the crude proteoglycans are treated in an aqueous medium with a base or a hypobromite, followed by removal of excess reactant and insoluble residues, the purified proteoglycans being present in aqueous solution.

In one embodiment of the process according to the present invention, the crude proteoglycans are treated with an aqueous alkali hydroxide, particularly sodium hydroxide solution having a molarity of from 0.05 to 2 M, preferably a molarity 0.1 M, the treatment being continued for a few hours, for example 24 hours, at a temperature which is close to ambient temperature, for example 25° C. The treatment is preferably carried out with stirring. The effect of the above treatment is to hydrolyze the proteoglycans in controlled manner in order to extract the soluble fraction therefrom.

In order to eliminate the excess reactant in this embodiment, the hydrolysate is neutralised with an acid, such as hydrochloric acid, and the salt thus formed is eliminated, for example by dialysis against distilled water. This leaves an insoluble residue which may be eliminated by precipitation and, more advantageously, by centrifuging, for example for 45 minutes at 30,000 g and at 4° C.

The supernatant phase obtained constitutes the purified soluble proteoglycans.

In a second embodiment of the process according to the present invention, the crude proteoglycans in water are treated with an alkali hypobromite for a period of the order of a few tens of minutes, preferably at ambient temperature and with stirring, after which time the excess hypobromite may be eliminated, preferably by dialysis for 24 hours against running water and then against distilled water. The insoluble residue may be eliminated as described above.

In addition, the process according to the present invention preferably further comprises a step in which the lipids A are eliminated by acid hydrolysis in an aqueous medium, preferably at a temperature in the range of from 70° to 100° C. and in the presence of approximately 1% of glacial acetic acid for a period of the order of 90 minutes, followed by elimination of the thus formed precipitate.

The present invention also provides purified, water-soluble bacterial membranal proteoglycans as an immunity adjuvant in vaccines, having the following composition by weight:

| | |
|---|---|
| hexoses | 24-42% |
| proteins | 31-53% |
| lipids | 12-18% |
| hexosamines | 2-6% |
| RNA | <0.5% |
| DNA | <0.2% |
| LPS | <0.001% |

Of these proteoglycans, particular reference is made to those having the following compositions:

| | |
|---|---|
| hexoses | 37 ± 5% |
| proteins | 36.5 ± 5% |
| lipids | 15 ± 3% |
| hexosamines | 5 ± 2% |
| RNA | <0.5% |
| DNA | <<0.2% |
| LPS | <0.001% | and which may be obtained in particular by the above-described process using an alkali hydroxide.

Among the proteoglycans according to the present invention, reference is also made to those having the following composition:

| | |
|---|---|
| hexoses | 29 ± 5% |
| proteins | 48 ± 5% |
| lipids | 15 ± 3% |
| hexosamines | 4 ± 2% |
| RNA | <0.5% |
| DNA | <<0.2% |

| | |
|---|---|
| -continued | |
| LPS | <0.001% | which may be obtained in particular by the above-described process using a hypobromite.

The various fractions may be characterised by the following analytical methods:

Hexoses: by the reaction with anthrone according to SCOTT (T. A.), MELVIN (E. H.), 1953, Analyt. Chem. 25, 1956.

Proteins: by the biuret reaction according to GORNALL (A. G.), BARDAXILL (C. A.), DAVID (V. V.), 1949, J. Biol. Chem. 177,751

Lipids: by a gravimetric method based on global extraction with organic solvents.

Hexosamines: by their reaction with p-dimethyl amino benzaldehyde according to MORGAN (W. T. S.), RONDELL (C. J. M.), 1955, Biochem. J.61

RNA (ribonucleic acid): by direct UV spectrophotometry at 260 nm and by the orcinol reaction according to LUSENA (C. V.), 1951, Canad. J. Biochem. 29, 107–108

DNA (desoxy ribonucleic acid): by the coloured diphenyl amine reaction according to BURTON (K.), 1956, Biochem. J. 62,315.

LPS (lipopolysaccharides): by the coloured carbocyanine reaction described by JANDA (J.), WORK (E.), 1971, FEBS Letters, Vol. 16, number 4, pages 343–345.

Residual water: by the Karl FISCHER reaction.

In general, the crude membranal proteoglycans to be purified may be prepared by any known process and, more particularly, by the process described in the above-mentioned French Patent or by fractional centrifuging from a ground bacterial biomass in order to sediment successively the cell debris at an acceleration of preferably from 7000 to 8000 g for a few minutes and then the membranes at an acceleration of from 20,000 to 40,000 g for a few tens of minutes, followed by separation of the proteoglycans from the membranes by fractional centrifugation in saline solution and in water.

The following scheme is one example of how purified proteoglycans are obtained from a bacterial biomass.

Schematic Illustration of the Preparation of Proteoglycans:

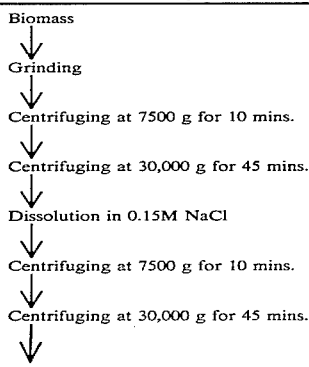

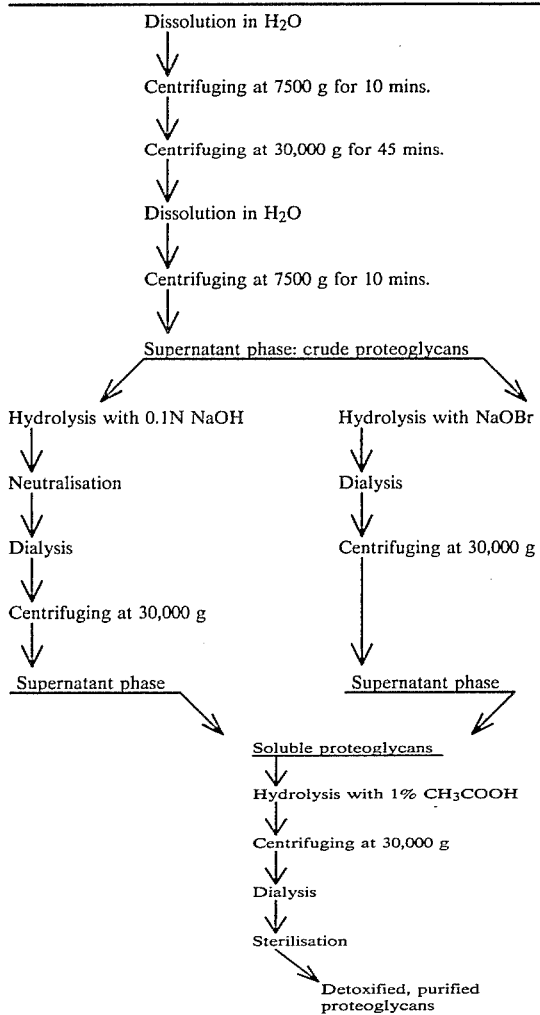

Those membranal proteoglycans according to the present invention which are of particular interest are extracted from membranes of gram-negative bacteria, more particularly from those of the geni Klebsiella, Serratia and Escherichia and, above all, *Klebsiella pneumoniae, Serratia marcescens* and *Escherichia coli.*

The present invention also relates to vaccines containing the membranal proteoglycans described above, and, more particularly, to vaccines containing as immunogenic fraction ribosomes or RNA's extracted from pathogenic bacteria against which it is desired to obtain immunity.

The RNA's and ribosomes suitable for use in the vaccines according to the present invention may be prepared by known processes and, in particular, by the processes described in French Pat. Nos. 73 43957, 75 10252 and 76 24124.

In one embodiment of this aspect of the present invention, the ratio by weight between the immunogenic fraction and the proteoglycans according to the present invention amounts to between 1.4 and 1.6 and preferably to 1.5.

Reference is made in particular to the following vaccines:

| (1) Broncho-ORL vaccines | |
|---|---|
| (a) Ribosome/proteoglycan association | |
| ribosomes of *Klebsiella pneumoniae* | 3.5 µg |
| ribosomes of *Streptococcus pneumoniae* | 3.0 µg |
| ribosomes of *Streptococcus pyogenes* $A_{12}$ | 3.0 µg |
| ribosomes of *Hemophilus influenzae* | 0.5 µg |
| proteoglycans of *Klebsiella pneumoniae* | 15.0 µg |
| (b) Ribosomal RNA/proteoglycan association: | |
| ribosomal RNA of *Klebsiella pneumoniae* | 2.45 µg |
| ribosomal RNA of *Streptococcus pneumoniae* | 2.10 µg |
| ribosomal RNA of *Streptococcus pyogenes* $A_{12}$ | 2.10 µg |
| ribosomal RNA of *Hemophilus influenzae* | 0.35 µg |
| proteoglycans of *Klebsiella pneumoniae* | 10.50 µg |
| (2) Anti-pyorrhoeal vaccines | |
| (a) Ribosomes/proteoglycans association | |
| ribosomes of *Rothia dentocariosus* | 1.2 µg |
| ribosomes of *Actinomyces viscosus* | 1.2 µg |
| ribosomes of *Streptococcus mutans* | 0.8 µg |
| ribosomes of *Streptococcus salivarius* | 2.0 µg |
| ribosomes of *Lactobacillus casei* | 1.2 µg |
| proteoglycans of *Klebsiella pneumoniae* | 9.6 µg |
| (b) Ribosomal RNA/proteoglycan association: | |
| ribosomal RNA of *Rothia dentocariosus* | 0.84 µg |
| ribosomal RNA of *Actinomyces viscosus* | 0.84 µg |
| ribosomal RNA of *Streptococcus mutans* | 0.56 µg |
| ribosomal RNA of *Streptococcus salivarius* | 1.40 µg |
| ribosomal RNA of *Lactobacillus casei* | 0.84 µg |
| proteoglycans of *Klebsiella pneumoniae* | 6.72 µg |
| (3) Dermatological anti-acne vaccine | |
| (a) Ribosome/proteoglycan association: | |
| ribosomes of *Corynebacterium acnes* | 2 µg |
| ribosomes of *Corynebacterium parvum* | 2 µg |
| ribosomes of *Streptococcus pyogenes* | 2 µg |
| ribosomes of *Staphylococcus epidermidis* | 2 µg |
| proteoglycans of *Serratia marcescens* | 12 µg |
| (b) Ribosomal RNA/proteoglycan association: | |
| ribosomal RNA of *Corynebacterium acnes* | 1.4 µg |
| ribosomal RNA of *Corynebacterium parvum* | 1.4 µg |
| ribosomal RNA of *Streptococcus pyogenes* | 1.4 µg |
| ribosomal RNA of *Staphylococcus epidermidis* | 1.4 µg |
| proteoglycans of *Serratia marcescems* | 8.4 µg |
| (4) Gynaecological vaccine | |
| (a) Ribosome/proteoglycan association | |
| ribosomes of *Escherichia coli* | 2 µg |
| ribosomes of *Streptococcus faecalis* | 2 µg |
| ribosomes of Streptococcus H | 2 µg |
| ribosomes of *Staphylococcus epidermidis* | 2 µg |
| ribosomes of *Candida albicans* | 2 µg |
| proteoglycans of *Escherichia coli* | 15 µg |
| (b) Ribosomal RNA/proteoglygan association | |
| ribosomal RNA of *Escherichia coli* | 1.4 µg |
| ribosomal RNA of *Streptococcus faecalis* D | 1.4 µg |
| ribosomal RNA of Streptococcus H | 1.4 µg |
| ribosomal RNA of *Staphylococcus epidermidis* | 1.4 µg |
| ribosomal RNA of *Candida albicans* | 1.4 µg |
| proteoglycans of *Escherichia coli* | 10.5 µg |
| (5) Intestinal anti-typhus vaccine | |
| (a) Ribosome/proteoglycan association | |
| ribosomes of *Bacterium coli* | 2 µg |
| ribosomes of *Salmonella paratyphi* A | 2 µg |
| ribosomes of *Salmonella paratyphi* B | 2 µg |
| ribosomes of *Shigella dysenteria* | 2 µg |
| ribosomes of Enterococcus | 2 µg |
| proteoglycans of *Serratia marcescens* | 15 µg |
| (b) Ribosomal RNA/proteoglycan association | |
| ribosomal RNA of *Bacterium coli* | 1.4 µg |
| ribosomal RNA of *Salmonella paratyphi* A | 1.4 µg |
| ribosomal RNA of *Salmonella paratyphi* B | 1.4 µg |
| ribosomal RNA of *Shigella dysenteriae* | 1.4 µg |
| ribosomal RNA of Enterococcus | 1.4 µg |
| proteoglycans of *Serratia marcescens* | 10.5 µg |

EXAMPLE 1

Preparation of crude membranal proteoglycans of *K. pneumoniae*

The strain of *K. pneumoniae* is cultured on a medium containing (per liter):

| Meat extract | 5 g |
|---|---|
| Yeast extract | 5 g |
| Sucrose | 2 g |
| Disodium phosphate | 2.5 g |

After culturing the cells are separated from the culture medium by centrifuging, washed with a saline solution (NaCl), dried and optionally stored at $-20°$ C.

The biomass obtained by fermentation is concentrated and washed by continuous centrifuging. The bacterial concentrate thus obtained is dispersed in physiological serum to a final concentration of dry cells of 50 g per liter (as measured by spectrophotometry).

The bacterial suspension is subjected to cell grinding by passage through an APV-Manton Gaulin homogeniser equipped with special disintegration valves. During this operation, the temperature of the suspension is kept below 10° C.

The crude proteoglycans are isolated from this cell suspension by a series of differential centrifuging operations carried out under the following conditions:

Centrifuging for 10 minutes at 7500 g and 4° C. enables the unground cells and cell debris to be eliminated. The supernatant phase is then centrifuged for 45 minutes at 30,000 g and 4° C. to sediment the crude membranal fraction.

The 30,000 g deposit is dispersed by means of a homogenizer in 1 volume of cold 0.15 M NaCl and then subjected to the same cycle of centrifuging operations at 7500 g and 30,000 g as described above.

The 30,000 g deposit is then taken up this time in 1 volume of distilled water and dispersed to complete homogeneity.

The suspension in distilled water is again subjected to a cycle of centrifuging operations at 7500 g and 30,000 g, after which the deposit is taken up this time in one quarter of the initial volume of distilled water. The suspension is centrifuged for 10 minutes at 7500 g and the supernatant phase containing the crude proteoglycans is conserved.

EXAMPLE 2

To the preceding supernatant phase obtained in Example 1 containing the crude proteoglycans is added 1 ml of sodium hydroxide (10 N) per 100 ml of supernatant phase so as to obtain a final molarity of 0.1 M of NaOH.

The whole is then incubated for 24 hours at 25° C. with moderate stirring in order to extract the soluble fraction from the proteoglycans by controlled hydrolysis.

The hydrolysate is then neutralised with a 3 N solution of hydrochloric acid and the sodium chloride formed is eliminated by dialysis against distilled water.

The insoluble residue is eliminated after dialysis by centrifuging for 45 minutes at 30,000 g and 40° C. and the supernatant phase containing the soluble proteoglycans is conserved.

EXAMPLE 3

Preparation of purified proteoglycans

To the supernatant phase obtained in Example 1 containing the crude proteoglycans is added 2 ml of sodium hypobromite (10 ml of bromine + 60 ml of concentrated sodium hydroxide) per 100 ml of supernatant phase.

The suspension is then stirred for 30 minutes at ambient temperature, and after this time the excess hypobromite is eliminated by dialysis for 24 hours against running water and then against distilled water.

The insoluble residue is eliminated after dialysis by centrifuging for 45 minutes at 30,000 g and 4° C. and the supernatant phase containing the soluble proteoglycans is conserved.

EXAMPLE 4

The proteoglycans prepared in accordance with Example 2 are not completely detoxified, since they still contain small quantities of lipopolysaccharides having a hyperthermal effect. It is for this reason that the proteoglycans of Example 2 are treated as follows:

1 ml of glacial acetic acid is added to 100 ml of dialysed supernatant phase containing the soluble proteoglycans, followed by heating for 90 minutes to a temperature of 90° C.

This hydrolysis quantitatively separates the lipid A from the LPS and cooling in ice causes it to precipitate.

The precipitate of lipid A is eliminated by centrifuging for 20 minutes at 30,000 g and 0° C.

The supernatant phase is collected and then dialysed against distilled water for 24 hours to eliminate the acetic acid.

The dialysate is sterilised by filtration on a 0.22μ membrane and the filtrate is conserved in either frozen or freeze-dried form.

Its composition is as follows:

| | |
|---|---|
| Hexoses | 37 ± 5% |
| Proteins | 36.5 ± 5% |
| Lipids | 15 ± 3% |
| Hexosamines | 5 ± 2% |
| RNA | <0.5% |
| DNA | <<0.2% |
| LPS | <0.001% |

EXAMPLE 5

Proteoglycans having the following composition are obtained as in Example 4 from the purified proteoglycans of Example 3:

| | |
|---|---|
| Hexoses | 29 ± 5% |
| Proteins | 48 ± 5% |
| Lipids | 15 ± 3% |
| Hexosamines | 4 ± 2% |
| RNA | 0.5% |
| DNA | 0.2% |
| LPS | 0.001% |

The purified and detoxified proteoglycans are of course obtainable in analogous fashion from *Serratia marcescens* and *Escherichia coli* and may be used in the composition described above.

The vaccine formulations according to the present invention may of course be packaged with the supports and excipients known in the art according to their mode of application. The compositions described above are preferably injectable types.

The vaccines according to the present invention were tested for immunogenic activity and were found to have a considerably better activity than the vaccines described in French Pat. No. 73 43957 due to the replacement of the membranal proteoglycans by purified and detoxified membranal proteoglycans. However, the most advantageous aspect of the vaccines according to the present invention is that they have no pyrogenic effect.

A study of the pyrogenic effect was conducted as follows:

A dose of vaccine in 1 ml of water is injected intravenously into rabbits weighing from 2 to 2.5 kg and their rectal temperature is observed by thermocouple probe. The results obtained are set out in Table 1 below.

It can be seen that the vaccines according to the present invention are free from any pyrogenic effects.

| PYROGENIC EFFECT | | | | | |
|---|---|---|---|---|---|
| | Δ °C. | | | | |
| Batch Lot | 15' | 30' | 45' | 1 h | 1 h 15' |
| GN 153 | −0,03 | 0 | 0 | −0,016 | −0,05 |
| GN 155 | +0,06 | +0,05 | +0,83 | +1,05 | +1,16 |
| GN 156 | +0,06 | −0,04 | −0,06 | −0,16 | −0,20 |
| | Δ °C. | | | | |
| Batch Lot | 1 h 30' | 1 h 45' | 2 h | 2 h 30' | 3 h |
| GN 153 | −0,03 | −0,03 | −0,03 | −0,10 | −0,10 |
| GN 155 | +1,16 | +1,11 | +1,06 | +1,43 | +1,66 |
| GN 156 | −0,26 | −0,26 | −0,30 | −0,40 | −0,46 |
| | Δ °C. | | | | |
| Batch Lot | 3 h 30' | 4 h | 4 h 30' | 5 h | 5 h 30' |
| GN 153 | 0 | −0,16 | −0,15 | −0,16 | −0,18 |
| GN 155 | +1,90 | +1,48 | +1,1 | +0,71 | +0,36 |
| GN 156 | −0,20 | −0,50 | −0,44 | −0,46 | −0,46 |

GN 153—Antipyorrhoeal vaccines 2a, the proteoglycans being prepared by process described in Example 4.
GN 156—Same vaccines except that the proteoglycans were prepared by the process described in Example 5.
GN 155—Same vaccines as before except that the proteoglycans were subjected only to complete delipidation with chloroform.

What is claimed is:

1. An immunity adjuvant for vaccines comprising purified water-soluble proteoglycans obtained by a process which comprises at least one step in which crude membranal proteoglycans of Klebsiella, Serratia or Escherichia are treated in an aqueous medium with a reactant selected from the group consisting of bases and hypobromites followed by removal of the excess reactant and the insoluble residue, said purified water-soluble proteoglycans having the following composition by weight:

| | |
|---|---|
| hexoses | 24–42% |
| proteins | 31–53% |
| lipids | 12–18% |
| hexosamines | 2–6% |
| RNA | <0.5% |
| DNA | <0.2% |
| LPS | <0.001% |

2. An adjuvant as set forth in claim 1 wherein the purified water-soluble proteoglycans have the following composition by weight:

| | |
|---|---|
| hexoses | 37 ± 5% |

-continued

| | |
|---|---|
| proteins | 36.5 ± 5% |
| lipids | 15 ± 3% |
| hexosamines | 5 ± 2% |
| RNA | <0.5% |
| DNA | <<0.2% |
| LPS | <0.001% |

3. An adjuvant as set forth in claim 1 wherein the purified water-soluble proteoglycans have the following composition by weight:

| | |
|---|---|
| hexoses | 29 ± 5% |
| proteins | 48 ± 5% |
| lipids | 15 ± 3% |
| hexosamines | 4 ± 2% |
| RNA | <0.5% |
| DNA | <<0.2% |
| LPS | <0.001% |

4. A vaccine based on bacterial ribosome and/or RNA as immunogenic agent containing as immunity adjuvant an effective amount of an adjuvant of the type set forth in claim 1.

5. A vaccine as set forth in claim 4 having the following composition:

| | |
|---|---|
| ribosomes of *Klebsiella pneumoniae* | 3.5 μg |
| ribosomes of *Streptococcus pneumoniae* | 3.0 μg |
| ribosomes of *Streptococcus pyogenes* A₁₂ | 3.0 μg |
| ribosomes of *Hemophilus influenzae* | 0.5 μg |
| proteoglycans of *Klebsiella pneumoniae* | 15.0 μg |

6. A vaccine as set forth in claim 4 having the following composition:

| | |
|---|---|
| ribosomal RNA of *Klebsiella pneumoniae* | 2.45 μg |
| ribosomal RNA of *Streptococcus pneumoniae* | 2.10 μg |
| ribosomal RNA of *Streptococcus pyogenes* A₁₂ | 2.10 μg |
| ribosomal RNA of *Hemophilus influenzae* | 0.35 μg |
| proteoglycans of *Klebsiella pneumoniae* | 10.50 μg |

7. A vaccine as set forth in claim 4 having the following composition:

| | |
|---|---|
| ribosomes of *Rothia dentocariosus* | 1.2 μg |
| ribosomes of *Actinomyces viscosus* | 1.2 μg |
| ribosomes of *Streptococcus mutans* | 0.8 μg |
| ribosomes of *Streptococcus salivarius* | 2.0 μg |
| ribosomes of *Lactobacillus casei* | 1.2 μg |
| proteoglycans of *Klebsiella pneumoniae* | 9.6 μg |

8. A vaccine as set forth in claim 4 having the following composition:

| | |
|---|---|
| ribosomal RNA of *Rothia dentocariosus* | 0.84 μg |
| ribosomal RNA of *Actinomyces viscosus* | 0.84 μg |
| ribosomal RNA of *Streptococcus mutans* | 0.56 μg |
| ribosomal RNA of *Streptococcus salivarius* | 1.40 μg |
| ribosomal RNA of *Lactobacillus casei* | 0.84 μg |
| proteoglycans of *Klebsiella pneumoniae* | 6.72 μg |

9. A vaccine as set forth in claim 4 having the following composition:

| | |
|---|---|
| ribosomes of *Corynebacterium acnes* | 2 μg |
| ribosomes of *Corynebacterium parvum* | 2 μg |
| ribosomes of *Streptococcus pyogenes* | 2 μg |
| ribosomes of *Staphylococcus epidermidis* | 2 μg |
| proteoglycans of *Serratia marcescens* | 12 μg |

10. A vaccine as set forth in claim 4 having the following composition:

| | |
|---|---|
| ribosomal RNA of *Corynebacterium acnes* | 1.4 μg |
| ribosomal RNA of *Corynebacterium parvum* | 1.4 μg |
| ribosomal RNA of *Streptococcus pyogenes* | 1.4 μg |
| ribosomal RNA of *Staphylococcus epidermidis* | 1.4 μg |
| proteoglycans of *Serratia marcescems* | 8.4 μg |

11. A vaccine as set forth in claim 4 having the following composition:

| | |
|---|---|
| ribosomes of *Escherichia coli* | 2 μg |
| ribosomes of *Streptococcus faecalis* | 2 μg |
| ribosomes of Streptococcus H | 2 μg |
| ribosomes of *Staphylococcus epidermidis* | 2 μg |
| ribosomes of *Candida albicans* | 2 μg |
| proteoglycans of *Escherichia coli* | 15 μg |

12. A vaccine as set forth in claim 4 having the following composition:

| | |
|---|---|
| ribosomal RNA of *Escherichia coli* | 1.4 μg |
| ribosomal RNA of *Streptococcus faecalis* D | 1.4 μg |
| ribosomal RNA of Streptococcus H | 1.4 μg |
| ribosomal RNA of *Staphylococcus epidermidis* | 1.4 μg |
| ribosomal RNA of *Candida albicans* | 1.4 μg |
| proteoglycans of *Escherichia coli* | 10.5 μg |

13. A vaccine as set forth in claim 4 having the following composition:

| | |
|---|---|
| ribosomes of *Bacterium coli* | 2 μg |
| ribosomes of *Salmonella paratyphi* A | 2 μg |
| ribosomes of *Salmonella paratyphi* B | 2 μg |
| ribosomes of *Shigella dysenteria* | 2 μg |
| ribosomes of Enterococcus | 2 μg |
| proteoglycans of *Serratia marcescens* | 15 μg |

14. A vaccine as set forth in claim 4 having the following composition:

| | |
|---|---|
| ribosomal RNA of *Bacterium coli* | 1.4 μg |
| ribosomal RNA of *Salmonella paratyphi* A | 1.4 μg |
| ribosomal RNA of *Salmonella paratyphi* B | 1.4 μg |
| ribosomal RNA of *Shigella dysenteriae* | 1.4 μg |
| ribosomal RNA of Enterococcus | 1.4 μg |
| proteoglycans of *Serratia marcescens* | 10.5 μg |

* * * * *